US012629163B2

(12) United States Patent
Hinding

(10) Patent No.: US 12,629,163 B2
(45) Date of Patent: May 19, 2026

(54) ULTRASONIC GENERATOR FOR SUPPLYING AN ELECTRICAL POWER, LITHOTRIPSY DEVICE FOR FRAGMENTING CALCULI, AND METHOD FOR OPERATING AND/OR CONTROLLING A LITHOTRIPSY DEVICE

(71) Applicant: KARL STORZ SE & Co. KG, Tuttlingen (DE)

(72) Inventor: Thomas Hinding, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 86 days.

(21) Appl. No.: 18/543,840

(22) Filed: Dec. 18, 2023

(65) Prior Publication Data

US 2024/0197343 A1 Jun. 20, 2024

(30) Foreign Application Priority Data

Dec. 20, 2022 (DE) ..................... 10 2022 134 059.7

(51) Int. Cl.
*A61B 17/22* (2006.01)
*A61B 17/00* (2006.01)

(52) U.S. Cl.
CPC .................. *A61B 17/22004* (2013.01); *A61B 2017/00141* (2013.01); *A61B 2017/00398* (2013.01); *A61B 2017/00681* (2013.01); *A61B 2560/02* (2013.01)

(58) Field of Classification Search
CPC .... A61B 17/22004; A61B 2017/00141; A61B 2017/00398; A61B 2017/00681;
(Continued)

(56) References Cited

U.S. PATENT DOCUMENTS 4,271,371 A * 6/1981 Furuichi ............... B06B 1/0253
331/25
5,588,592 A * 12/1996 Wilson ................ B05B 17/0607
239/4
(Continued)

FOREIGN PATENT DOCUMENTS

DE 102018101215 A1 7/2019
EP 3733313 A1 11/2020
(Continued)

OTHER PUBLICATIONS

Anonymous "Protecting Devices from ESD Damage" Available at https://web.archive.org/web/20160413191215/http://electronicsbeliever. com/protecting-devices-from-esd-damage/; Posted Mar. 14, 2015.

*Primary Examiner* — Hien N Nguyen
(74) *Attorney, Agent, or Firm* — Jason H. Vick; Amped IP LLC

(57) ABSTRACT

The invention relates to an ultrasonic generator for supplying an electrical power for fragmenting calculi, the ultrasonic generator being assignable a sonotrode, an ultrasonic vibration excitation means for exciting a vibration of the at least one sonotrode, and optionally a force generation apparatus for generating a force for moving a projectile for shock excitation of the sonotrode, with the ultrasonic vibration excitation means being excitable at a vibration frequency by means of the ultrasonic generator by supplying an AC voltage, and the ultrasonic generator comprising a measuring apparatus with at least one measuring unit for measuring a time profile of a voltage and/or current, and an open-loop and/or closed-loop control apparatus for adjusting an electrical power suppliable by the ultrasonic generator to the
(Continued)

ultrasonic vibration excitation means, with the measuring apparatus comprising at least one resistor arranged in parallel with the at least one measuring unit and optionally a capacitor arranged in parallel with the measuring unit, wherein the measuring apparatus comprises, in parallel with the at least one measuring unit, at least one suppressor diode for suppressing overvoltage. The invention also relates to a lithotripsy device and a method for operating and controlling a lithotripsy device.

12 Claims, 3 Drawing Sheets

(58) Field of Classification Search
CPC ........ A61B 2560/02; A61B 17/320068; A61B 2017/00017; A61B 2017/00039; A61B 2017/00106; A61B 2017/0011; A61B 2017/22011; A61B 2017/22014; A61B 17/22012

See application file for complete search history.

(56) References Cited

U.S. PATENT DOCUMENTS

| | | | |
|---|---|---|---|
| 11,653,152 B1 * | 5/2023 | Lahoud | B06B 1/0215 310/311 |
| 2002/0010477 A1 * | 1/2002 | Hirt | A61B 17/22012 606/128 |
| 2002/0010486 A1 * | 1/2002 | Hirt | A61B 17/22012 606/169 |
| 2003/0045887 A1 * | 3/2003 | Sakurai | A61B 17/320092 606/128 |
| 2012/0136279 A1 * | 5/2012 | Tanaka | A61B 17/320092 601/2 |
| 2014/0269972 A1 * | 9/2014 | Rada | H04L 27/106 375/285 |
| 2015/0088154 A1 * | 3/2015 | Vaitekunas | B06B 1/0269 606/128 |
| 2015/0355237 A1 * | 12/2015 | Kutzner | G01R 1/36 324/110 |
| 2021/0038238 A1 | 2/2021 | Bionda et al. | |

FOREIGN PATENT DOCUMENTS

| | | |
|---|---|---|
| EP | 3082625 B1 | 10/2021 |
| WO | WO 2015/047628 A1 | 4/2015 |

* cited by examiner

ULTRASONIC GENERATOR FOR SUPPLYING AN ELECTRICAL POWER, LITHOTRIPSY DEVICE FOR FRAGMENTING CALCULI, AND METHOD FOR OPERATING AND/OR CONTROLLING A LITHOTRIPSY DEVICE

CROSS-REFERENCE TO RELATED APPLICATIONS

This application claims the benefit under 35 U.S.C. 119(a) to German Patent Application No. 10 2022 134 059.7, filed 20 Dec. 2022, the disclosure of which is incorporated herein by reference in its entirety.

BACKGROUND

The invention relates to an ultrasonic generator for supplying an electrical power for fragmenting calculi, the ultrasonic generator being assignable a sonotrode, an ultrasonic vibration excitation means for exciting a vibration of the at least one sonotrode, and optionally a force generation apparatus for generating a force for moving a projectile for shock excitation of the sonotrode, with the ultrasonic vibration excitation means being excitable at a vibration frequency by means of the ultrasonic generator by supplying an AC voltage, and the ultrasonic generator comprising a measuring apparatus with at least one measuring unit for measuring a time profile of a voltage and/or current, and an open-loop and/or closed-loop control apparatus for adjusting an electrical power suppliable by the ultrasonic generator to the ultrasonic vibration excitation means, with the measuring apparatus comprising at least one resistor arranged in parallel with the at least one measuring unit and optionally a capacitor arranged in parallel with the measuring unit. The invention also relates to a lithotripsy device for fragmenting and/or removing calculi and a method for operating and/or controlling a lithotripsy device.

Lithotripsy is a known method for fragmenting calculi which form, for example, through condensation and/or crystallization of salts and proteins in body organs, such as in the bladder or kidneys. If the calculi are too large to be passed naturally and causes discomfort, they have to be fragmented with a lithotripter so that the fragmented stones can be removed by natural excretion and/or by means of an aspiration/irrigation pump. The calculi to be subject to fragmentation are frequently structured inhomogeneously with different constituent parts and/or solidities.

To improve calculi fragmentation performance, use is made, especially in intracorporeal lithotripsy, of combination systems which combine two different excitation and/or vibration sources. To this end, intermittent, ballistic shockwave energy is frequently supplied in addition to the constant ultrasonic energy. For example, this can be implemented by means of a ballistic drive with electromagnets, in which an impact body is accelerated by means of the electromagnets and strikes on a horn and/or the sonotrode head. In pneumatic lithotripters, the projectile is instead accelerated within an acceleration tube by supplying compressed air and the kinetic energy of the projectile is transmitted via an elastic shock to the proximal end of the sonotrode and onward to the distal end of the latter for fragmenting a calculus. In a combined lithotripsy device, it is usual for a pneumatic unit to be able to be used advantageously for the fragmentation of hard stones and an ultrasonic unit to be able to be used for the fragmentation of soft stones.

For an effective and stable operation of the sonotrode in resonance, it is generally necessary for all components of the lithotripsy system, from the sonotrode via the ultrasonic transducer with the horn, the transmitter, and the ultrasonic generator, to be matched to one another. For closed-loop control of the ultrasonic unit, the voltage and the current at the piezo elements of the ultrasonic transducer are usually detected, rectangular signals are generated from the two sinusoidal signals by means of a comparator, and these rectangular signals are compared. The operating frequency—usually around 27 kHz—is corrected during the operation of the ultrasonic generator until the rectangular signals of current and voltage are in phase. As a result of heating and mechanical and/or electronic disruptions, the frequency must be constantly corrected by means of the ultrasonic generator in order to keep this in phase and ensure optimal operation of the sonotrode. During a combined operation, the ballistically and/or pneumatically driven projectile impacts on a distal-side abutment element and/or on the sonotrode and this mechanical shock is also transmitted to the piezo elements of the ultrasonic transducer, and these subsequently generate a very high voltage. As a result, the measurement of voltage and current and the determination of the phase shift for controlling the frequency in the ultrasonic generator are interfered with and/or no longer performable. As a result of the impact of the projectile not only on the sonotrode but also on the piezo element generating the ultrasonic waves, the very high voltage of the piezo element generated thereby is transmitted back and induces, in the ultrasonic generator, a voltage that disrupts the resonant frequency of the ultrasonic generator. Accordingly, the fragmentation power of the sonotrode by means of the ultrasonic excitation is undesirably reduced at the same time on account of the shock excitation.

The practice of operating an ultrasonic generator at a constant frequency in order to reduce a disruption of the ultrasonic generator on account of the mechanical impact of a projectile is well known. However, this leads to performance losses in the case of heating, mechanical and/or electronic disruptions, and detuning of the adjusted lithotripsy system. The electrical power supplied to the piezo elements of the ultrasonic transducer can be increased in order to compensate for these losses. Although this can partly compensate for the loss of performance, the effectiveness of the stone fragmentation remains reduced.

DE 10 2018 101 215 A1 has disclosed a device for fragmenting a calculus, having a first drive apparatus for periodic deflection and a second drive apparatus for impulse-type deflection of a probe, in which damage to the first drive apparatus is reduced by decoupling from the second drive apparatus by means of a transmission region in the form of a low-pass filter for frequency-selective transmission of vibrations. The transmission region is configured as a cross-sectional jump and/or as cross-sectional tapering. In the transmission direction, the cross-sectional tapering is formed from the first drive apparatus to a vibrating part of the first drive apparatus which acts on the probe, whereby as much of the impulse-type vibration from the second drive apparatus as possible is reflected. A disadvantage here is that, in the region of the cross-sectional tapering, spacing and/or clear space is required both in the longitudinal direction of the probe and transversely to the probe, and this increases the installation space or at least prevents efficient use of the installation space available.

A further disadvantage of known countermeasures is that mutual influencing between a ballistic unit and the ultrasonic unit is usually only minimized directly, and these do not act in the case of a disadvantageous transmission back to the ultrasonic generator and do not allow controllability of the operating frequency of the ultrasonic generator.

It is an object of the invention to improve the prior art.

This object is achieved by an ultrasonic generator for supplying an electrical power for fragmenting calculi, the ultrasonic generator being assignable a sonotrode, an ultrasonic vibration excitation means for exciting a vibration of the at least one sonotrode, and optionally a force generation apparatus for generating a force for moving a projectile for shock excitation of the sonotrode, with the ultrasonic vibration excitation means being excitable at a vibration frequency by means of the ultrasonic generator by supplying an AC voltage, and the ultrasonic generator comprising a measuring apparatus with at least one measuring unit for measuring a time profile of a voltage and/or current, and an open-loop and/or closed-loop control apparatus for adjusting an electrical power suppliable by the ultrasonic generator to the ultrasonic vibration excitation means, with the measuring apparatus comprising at least one resistor arranged in parallel with the at least one measuring unit and optionally a capacitor arranged in parallel with the measuring unit, and with the measuring apparatus comprising, in parallel with the at least one measuring unit, at least one suppressor diode for suppressing overvoltages.

Hence, an ultrasonic generator for a lithotripsy device is provided, in which, on account of the specifically designed measuring device, back-transmitted voltage peaks generated by a piezo element, for example caused by a shock excitation by a projectile, are suppressed in the assigned ultrasonic vibration excitation means. This allows a measurement of a time profile of a voltage and/or current by means of the measuring apparatus despite mechanical and/or electrical disruptions and allows an adjustment of the electrical power and/or frequency supplied by the ultrasonic generator to the ultrasonic vibration excitation means. Consequently, the measuring apparatus is protected from overvoltage generated by the ultrasonic vibration excitation means and/or piezo element. This provides an ultrasonic generator for a combined lithotripsy device with an ultrasonic unit operating without problems and a ballistic and/or pneumatic unit for shock excitation, in which the fragmentation performance of the shock excitation can be maximized without impairing the function of the ultrasonic generator and/or ultrasonic unit.

As a result of the ultrasonic generator comprising the measuring apparatus, voltage and/or current are measured on the primary side of the transmitter to the ultrasonic vibration excitation means, whereby the measuring unit of the measuring apparatus is electrically isolated from the piezo element or the piezo elements of the ultrasonic vibration excitation means and a back-transmission to the ultrasonic generator is at least reduced.

On account of the damping of the measured signal by the resistor and an interference suppression by means of the suppressor diode which eliminates or at least minimizes interfering voltage peaks, the measuring apparatus is largely operable in reliable fashion, even in the case of mechanical and/or electrical disruptions and/or a shock excitation by means of the projectile. As a result, the suppressor diode of the measuring apparatus can remove, at least in part, briefly occurring voltage peaks, for example of 1000 V, generated by the piezo element of the ultrasonic transducer on account of a shock excitation, and hence the measuring unit connected in parallel can be protected. If, in the case of very severe disruptions, a measurement of voltage and/or current and the determination of the presence of both in phase are not possible despite this protection of the measuring apparatus, then this brief state can be bridged by means of the open-loop and/or closed-loop control apparatus by virtue of using known values of the resonant frequency. As a result, the ultrasonic vibration excitation means operates substantially in resonance and there is a high fragmentation performance at optimal efficiency.

An essential concept of the invention is based on a mechanical and/or electrical disruption of the ultrasonic vibration excitation means and/or the negative influence of the piezo element of the ultrasonic vibration excitation means as a result of the shock excitation by a projectile precisely not being implemented by structural, mechanical configuration of the ultrasonic vibration excitation means but by electronic filtering and/or damping of the disruptions and/or overvoltage pulses by means of the measuring apparatus of the ultrasonic generator itself, and the measurement signals obtained thus subsequently being analyzable by means of the open-loop and/or closed-loop control apparatus and being optimally usable for the operation of the ultrasonic generator. This ensures that the ultrasonic transducer operates in resonance and its fragmentation performance is not impaired by a shock excitation by means of a projectile. Consequently, an optimal power supply to the sonotrode and a good respective fragmentation performance of the vibration excitation by means of the ultrasonic transducer and shock excitation by means of the projectile are obtained, even in a combined lithotripsy system.

The following concepts shall be explained:

A "lithotripsy device" (also called a "lithotripter") is in particular a device for fragmenting calculi by shocks, shock waves, deformation waves, and/or vibration waves. A lithotripsy device is understood to include, in particular, various structural parts, constructional and/or functional components of a lithotripter The lithotripsy device can completely or partially form a lithotripter. A lithotripsy device can be in particular be an intracorporeal or extracorporeal lithotripsy device. In the case of an intracorporeal lithotripsy device, the latter can additionally comprise an irrigation/aspiration pump. The lithotripsy device can be designed as hand-held equipment and/or can comprise an endoscope or be inserted into an endoscope. The lithotripsy device is in particular autoclavable and has, for example, instrument steel and/or plastic. The lithotripsy device can comprise further components, such as control and/or supply equipment, or this is assigned to the lithotripsy device. In particular, a lithotripsy device is a combined lithotripsy device with a ballistic and/or pneumatic unit and an assignable force generation apparatus and with an ultrasonic vibration excitation means. By way of a shock energy when a projectile strikes a distal-side abutment element, a deformation wave shaped in a targeted manner is impressed directly or indirectly on the sonotrode, in particular, by means of the ballistic and/or pneumatic unit and the assignable force generation device. The deformation wave causes in particular a translational movement of the sonotrode, which causes fragmentation of stones on account of the deflection. In addition to the mechanical shock, the sonotrode in the combined lithotripsy device is excited to vibrate at the same time, in particular as a longitudinal vibration and/or transverse vibration, in particular by means of an ultrasonic vibration excitation means. Thus, the sonotrode is designed in particular as a waveguide for the vibration waves generated by the ultrasonic vibration excitation means and for the deformation waves of the projectile.

The term "calculi" (also referred to as "concretions") refers in particular to all stones in a human or animal body, which are formed for example from salts and proteins by crystallization and/or condensation. The calculi can include gallstones, urinary stones, kidney stones and/or salivary stones. As a result of the sonotrode and/or hollow probe acting on the calculi, calculus cores (also referred to as drilled cores) and/or calculus fragments in particular arise.

A "carrier unit" (also referred to as a "handpiece") is a grip and/or holding part of the lithotripsy device in particular. The carrier unit can be in particular a handle for manual and/or automated operation and/or connection of the lithotripsy device. A carrier unit can also be arranged at, connected to and/or guided in an automated manner at a distal end of a robot arm. In particular, the carrier unit has a housing. The carrier unit can also be formed from two or more parts. For example, the carrier unit may comprise a separate housing for a pneumatic unit and a separate housing for the ultrasonic vibration excitation means.

The terms "distal-side" and "distal" refer to an arrangement close to the patient's body and thus remote from the user, and/or a corresponding end or section. Accordingly, "proximal-side" or "proximal" refers to an arrangement close to the user and thus remote from the patient's body, or a corresponding end or section.

A "sonotrode" is in particular a component which, by the action and/or introduction of mechanical vibrations, is itself set in vibration and/or resonant vibration. In particular, the sonotrode is designed as a waveguide for the vibration waves generated by the ultrasonic vibration excitation means and for the deformation waves resulting from the impact of the projectile accelerated by means of the force generation apparatus. In particular, the sonotrode is directly or indirectly connected to the ultrasonic vibration excitation means and/or the horn. For example, the sonotrode is screwed into the distal-side end of the horn. The sonotrode comprises a sonotrode head, in particular at its proximal end, for recording, transmitting, and/or focusing ultrasonic waves and a sonotrode tip, at its distal end, for directly and/or indirectly impacting on and/or contacting calculi. The sonotrode is in particular shaped in such a way that it optimally introduces the vibration waves, the ultrasonic vibration, and the deformation waves at its distal end into the body, into the region of the body to be treated, and/or directly onto the calculus to be fragmented in the body. In the case of ultrasonic excitation, the sonotrode operates in particular in the ultrasonic range with a frequency range from 20 kHz to 90 kHz, preferably from 20 kHz to 34 kHz. In particular, the sonotrode comprises steel, titanium, aluminum, and/or carbon. In particular, a sonotrode is a probe with for example a bar-shaped, tube-shaped, and/or hose-shaped embodiment. The sonotrode can be formed in one or more pieces. The sonotrode has in particular a diameter in a range of 0.5 mm to 4.5 mm, in particular of 0.8 mm to 3.8 mm.

A "projectile" is in particular a body which is freely movable along the acceleration path within a cavity in an acceleration tube. The projectile is movable in particular back and forth between the proximal-side abutment element and a distal-side abutment element within the cavity, arranged therebetween, in the acceleration tube. In principle, the projectile can have any shape. For example, the projectile can have the shape of a bolt or a ball. The projectile has in particular hard steel and/or weak magnetic properties. For the free mobility, the projectile has in particular a slightly smaller outer diameter than the diameter of the cavity in the acceleration tube. For example, the projectile can have an outer diameter of 8 mm, in particular 6 mm, or 4 mm.

In particular, the projectile can be moved back and/or forth along the acceleration path continuously or discontinuously by means of the force generation device. Preferably, the projectile is moved back and forth in an intermittent and/or oscillating manner between the proximal-side abutment element and the distal-side abutment element.

In principle, a "force generation apparatus" can be any type of apparatus that applies a force to the projectile and thus causes a movement of the projectile. The force generation apparatus can be, for example, an apparatus which accelerates the projectile by means of a laser, a pressure medium, for example pneumatically by means of compressed air, by means of an electromagnetic field and/or by means of a mechanical apparatus. A pneumatic force generation apparatus can bring about a linear motion of the projectile in the cavity in the acceleration tube by means of a supply and/or removal of a pressure medium in particular. In particular, the pressure medium flows into the cavity in the acceleration tube through at least one proximal-side opening in the acceleration tube and presses and accelerates the projectile in the distal direction.

An "acceleration tube" is in particular an elongated hollow body whose length has a greater dimension than its diameter. In its interior, the acceleration tube has a cavity in particular, in which a projectile can move freely in the longitudinal direction. Moreover, the acceleration tube in particular comprises a proximal end and a distal end which, minus the length of the projectile, spatially define the maximum acceleration path. Distally and/or at its distal end portion, the acceleration tube is surrounded, in particular at least in part, by the horn and/or a bolt connected to or associated with the horn. In the case of a pneumatic force generation apparatus, the acceleration tube comprises at least one opening for the entrance and/or exit of a pressure medium, in particular compressed air. As material, the acceleration tube comprises a metal in particular.

An "abutment element" in particular is in particular a desired endpoint of the movement of the projectile along the acceleration path within the cavity in the acceleration tube, at which the accelerated projectile impacts on the abutment element, is decelerated, and/or moved in the opposite direction. In particular, a distal-side abutment element is arranged at and/or in the distal end of the acceleration tube and/or within the cavity in a region of the distal portion of the acceleration tube. The distal-side abutment element transmits the shock of the projectile onto the sonotrode, in particular directly or indirectly. For example, the distal-side abutment element can be a proximal-side wall of the horn, a spring element, or a proximal-side wall of a holder for a spring element. In particular, a proximal-side abutment element is arranged at and/or in the proximal end of the acceleration tube or within the cavity in a proximal portion of the acceleration tube. For example, the proximal-side abutment element can be a wall of the housing, a receptacle for the acceleration tube, and/or a spring element.

In particular, an "ultrasonic generator" is a piece of electrical equipment for supplying an AC voltage to an ultrasonic vibration excitation means for the purpose of generating a resonant vibration in a sonotrode. The ultrasonic generator comprises in particular a power supply unit, a sine-wave generator, an electronic sampling unit and/or an oscillator and/or a transforming transmitter of the AC voltage. An AC voltage with changeable amplitude and/or frequency, in particular, is generated by means of the ultrasonic generator.

The "sine-wave generator" (also referred to as a "signal generator") is in particular a piece of electronic equipment, an assembly or a circuit which generates a voltage with a characteristic time profile. In particular, the generated AC voltage comprises a frequency range of from 20 kHz to 90 kHz, preferably 20 kHz to 34 kHz. The signal generator of the ultrasonic generator is connected, in particular electrically connected, to the ultrasonic vibration excitation means. The electrical power supplied by the sine-wave generator determines the amplitude in particular, and hence the vibration deflection of the sonotrode.

In particular, an "ultrasonic vibration excitation means" (also referred to as "vibration excitation means") is any apparatus for generating vibrations in the ultrasonic range. In particular, the ultrasonic vibration excitation means is a component of an ultrasonic transducer and/or handpiece of a lithotripsy device and serves to convert the supplied AC voltage at a specific frequency into a mechanical vibration frequency. In particular, the ultrasonic vibration excitation means is an electromechanical transducer that exploits the piezoelectric effect. As a result of applying the AC voltage generated by an ultrasonic generator, a mechanical vibration is generated on account of a deformation of at least one piezo element of the ultrasonic transducer. In particular, the ultrasonic transducer comprises a piezo element or two or more, preferably stacked piezo elements. Preferably, the ultrasonic vibration excitation means comprises at least two piezo elements, with an electrical conductor, for example a copper plate, being arranged between the piezo elements. A distal-side piezo element of the ultrasonic vibration excitation means is arranged, in particular directly arranged, at a proximal wall of a proximal horn. In particular, a counter bearing is arranged on the proximal side of the piezo element or piezo elements.

In particular, a "horn" is a component arranged between the ultrasonic vibration excitation means and/or a piezo element on the one hand and the sonotrode on the other hand. In particular, the horn serves to transfer the ultrasonic waves generated by the ultrasonic vibration excitation means to the sonotrode, to transmit, to focus, and/or to align said ultrasonic waves. To this end, the horn may taper in a transfer direction and directly or indirectly transfer the ultrasonic waves to a probe head. The horn can also be used for fastening the sonotrode. At the same time, the horn serves in particular together with a counter bearing for mechanically holding the piezo element or piezo elements on both sides. The counter bearing preferably is a reflector for the ultrasonic waves. At the same time, the counter bearing and the horn also serve as a mechanical holder for the acceleration tube, which is arranged in the longitudinal direction in the interior of the counter bearing and horn. In particular, the counter bearing and/or the horn comprise a cavity for accommodating the acceleration tube.

In particular, an "AC voltage" is a voltage whose polarity changes with regular repetition.

In particular, a "frequency" is a measure for the rate at which the repetitions follow one another in a periodic procedure. In particular, the frequency is the reciprocal of the period. In particular, the frequency specifies the number of periods of AC voltage cycled through in one second. In particular, a "resonant frequency" is a frequency in the excitation of the sonotrode at which the amplitude grows more strongly than in the case of an excitation with adjacent frequencies. In particular, the resonant frequency is the frequency at which the amplitude of a forced vibration is maximal. If a sonotrode has a plurality of natural frequencies, it has in particular a plurality of local maxima of the forced amplitude and hence a plurality of resonant frequencies. In particular, the "operating frequency" of the ultrasonic generator is the frequency at which a phase shift of zero between the profiles of voltage and current is determined or at which a specified value of the phase shift is present.

In particular, a "measuring apparatus" is a piece of equipment, an assembly, and/or a plurality of components with which the time profile of the voltage and/or current within the ultrasonic generator is measurable. In particular, a measuring apparatus comprises a measuring unit for measuring a time profile of the voltage and/or current, a resistor arranged in parallel with the measuring unit and at least one suppressor diode arranged in parallel and serving to suppress overvoltages. Optionally, the measuring apparatus may comprise a capacitor arranged in parallel with the measuring unit. In particular, the measuring apparatus measures the voltage directly while the voltage drop across a resistor, in particular a shunt resistor, is measured in a second channel, with this corresponding to the current. Likewise, a current clamp or a current measuring coil as a measuring unit on a connecting line between a sine-wave generator and the transmitter to the ultrasonic vibration excitation means can be used to measure the current within the ultrasonic generator.

In particular, a "suppressor diode" is an electronic component which passes current in one direction and blocks the flow of current in another direction. In particular, a suppressor diode serves to protect the electronic circuit of the measuring apparatus from brief voltage pulses. In particular, a suppressor diode becomes conductive when a component-specific voltage threshold is exceeded. In this case, the current of the voltage pulse is in particular guided through a parallel circuit past the component, in particular the measuring unit, to be protected. As a result, no destructive voltage above the breakdown voltage of the suppressor diode in particular can build up.

In particular, an "open-loop control apparatus" is understood to mean an apparatus which sets a specified value. In particular, a "closed-loop control apparatus" is understood to mean an apparatus which feeds back a measurement value and in each case sets a manipulated value. Consequently, the open-loop and/or closed-loop control apparatus can be used to set and/or control the optimal and/or admissible electrical power and/or frequency. The open-loop and closed-loop control apparatus may comprise an electronic sampling unit. In particular, an electronic sampling unit is a piece of electronic measuring equipment which records, digitizes, and/or on an electronic visual display renders visible a time profile of a voltage or a plurality of voltages. In particular, the electronic sampling unit has at least two channels. The electronic sampling unit need not necessarily comprise an electronic visual display for rendering the time profiles visible; instead, these data can be recorded and/or processed directly internally within the open-loop and/or closed-loop control apparatus and/or a data storing and/or data processing unit of the ultrasonic generator. An electronic sampling unit can be an oscilloscope, in particular a digital oscilloscope, with the oscilloscope being able to be integrated in, or assigned to, the ultrasonic generator.

In a further embodiment of the ultrasonic generator, the at least one measuring unit is a measuring coil and the measuring apparatus comprises the capacitor for forming a parallel resonant circuit and the resistor for damping a time profile of the voltage and/or current.

As a result of the capacitor being connected parallel to the measuring unit and/or the measuring coil for measuring the current and the size of the capacitance of the capacitor being chosen accordingly, the measuring unit and/or measuring coil and the capacitor form a resonant circuit at approximately 27 kHz in particular, which corresponds to the resonant frequency of the sonotrode.

In particular, a "capacitor" is a passive electrical component with which electric charge is able to be stored in an electric field. The charge stored per unit voltage is referred to as capacitance in particular. In an AC circuit, the capacitor acts in particular as an AC resistor with the frequency-dependent impedance value. In particular, the capacitor comprises two electrodes as electrically conductive areas, which are separated from one another by a dielectric as an insulating material. The size of the capacitance of the capacitor is determined in particular by the area of the electrodes, the material of the dielectric, and/or the spacing of the electrodes.

In order to easily determine the current by means of the measuring apparatus, the at least one measuring apparatus is a measuring resistor for measuring the time profile of the current.

Hence, a diverter resistor is connected in parallel with a part of the circuit. In particular, a measuring resistor can be a shunt resistor.

In particular, a "measuring resistor" (also referred to as "diverter resistor" or "shunt resistor") is an electrically conductive component which is connected in parallel with a part of a circuit in order to divert an electric current from this part. In particular, a measuring resistor is also a current resistor and hence a low-resistance electrical measuring resistor. In particular, the measuring resistor can be equipped with separate current and/or voltage terminals. The measuring resistor is directly inserted into a current-conducting line. In particular, only a small current, which is usually negligible, is diverted through a piece of voltage measuring equipment connected in parallel to such a measuring resistor.

In a further embodiment of the ultrasonic generator, the capacitor and the at least one measuring unit are embodied such that the parallel resonant circuit has a frequency ranging from 20 kHz to 40 kHz, in particular from 25 kHz to 35 kHz, preferably around 27 kHz.

A "parallel resonant circuit" (also referred to as "resonant circuit") is an electrical circuit, capable of resonance, made of a coil and/or measuring coil and a capacitor and capable of implementing electrical oscillations. In the parallel resonant circuit, energy is exchanged, in particular periodically exchanged, between the magnetic field of the coil and/or measuring coil and the electric field of the capacitor, whereby a high current intensity or high voltage is alternately present. The resonant frequency f0 of the parallel resonant circuit is calculated according to:

$$f_0 = \frac{1}{2\pi\sqrt{L \cdot C}}$$

where L represents the inductance of the coil and C represents the capacitance of the capacitor. If the parallel resonant circuit is periodically excited, especially in the region of its resonant frequency, then it performs forced oscillations. For example, if the capacitor has a capacitance C of 0.0068 pF and the coil has an inductance L of 0.0093 μH, then this yields a resonant frequency of 20 kHz. Consequently, the sinusoidal oscillation generated by the sine-wave generator can be measured by means of the parallel resonant circuit of the measuring apparatus and corrected by means of the open-loop and/or closed-loop control apparatus.

To determine the phase shift of voltage and current and correct the frequency, the open-loop and/or closed-loop control apparatus comprises two comparators for generating rectangular signals from the time profile of the current and voltage.

The rectangular signals generated by means of the two comparators are compared and the frequency of the AC voltage generated by the sine-wave generator is corrected and/or modified until the phase shift between current and voltage is zero or has reached a specified value. Instead of the open-loop and/or closed-loop control apparatus, an electronic sampling unit may also comprise the two comparators, or an electronic sampling unit with the two comparators is a constituent part of the open-loop and/or closed-loop control apparatus.

In particular, a "comparator" is an electronic circuit which compares two voltages. In particular, a signal indicating which of the two input voltages is higher is available at the output of the comparator. A comparator can be a Schmitt trigger and hence an electronic comparator circuit in which the switch-on and/or switch-off thresholds do not coincide but are offset from one another by a certain voltage. In particular, the Schmitt trigger serves to generate binary signals with steep signal flanks and/or to obtain unique switching states from an analog input signal profile loaded with disturbance injection. In particular, the Schmitt trigger carries out a comparison between an input voltage and one of two possible threshold voltages. As a result, the Schmitt trigger acts as a threshold value switch and, as output signal, generates rectangular signals when an upper threshold voltage is exceeded and a lower threshold voltage is undershot. Hence, the profiles of the rectangular signals generated by the two comparators and/or Schmitt triggers can be analyzed in terms of their phase shift.

In a further embodiment, the ultrasonic generator comprises a data storing and/or data processing unit, in which a previously determined frequency and/or resonant frequency of the assignable sonotrode is or are storable.

As a result, the determined resonant frequency of the connected sonotrode can be compared to a list of previous resonant frequencies stored in the ultrasonic generator. Additionally, a required or maximum power when using this sonotrode can likewise be stored with a predetermined value in the data storing and/or data processing unit. Moreover, a change of and/or damage to the sonotrode can be identified in a timely fashion by a comparison of the currently determined resonant frequency with the resonant frequency stored in the data memory, and the sonotrode can be replaced prior to the application. In particular, storing the previously determined operating frequency of the ultrasonic generator in the data storing and/or data processing unit allows this frequency to be retrieved and used if a disturbance is so large that, despite the resistor, the suppressor diode, and/or the capacitor arranged in parallel, the measuring apparatus is unable to measure the time profile of the voltage and current and unable to determine the phase shift, with a correction of the frequency by means of the ultrasonic generator not being possible as a consequence.

In order to optimally adjust and correct the frequency despite a disturbance by a shock excitation, the open-loop and/or closed-loop control apparatus comprises a phase locked loop unit such that the suppliable electrical power and/or the frequency are or is adjustable by means of the open-loop and/or closed-loop control apparatus such that a phase shift of the time profiles of the voltage and current is zero or has a specified value and/or, in the case of a shock excitation of the sonotrode by means of the projectile, the previously determined frequency and/or resonant frequency of the suppliable electrical power is specifiable.

In particular, a "phase locked loop unit" (also referred to simply as "phase locked loop") is a control loop with a controlled oscillator, the phase of which is corrected to that of an external signal. In the case of the phase locked loop, the dependence of the manipulated variable on the system deviation and hence the phase shift is periodic in particular. In particular, the closed-loop control can latch onto different relative phase angles. In the latched-on state, the frequency of the oscillator is the frequency of the control signal in particular.

In a further aspect of the invention, the object is achieved by a lithotripsy device for fragmenting and/or removing calculi, with the lithotripsy device comprising an ultrasonic generator, a carrier unit with an ultrasonic vibration excitation means and a sonotrode that is connectable distally to the carrier unit, the ultrasonic generator being electrically connectable to the carrier unit, and the ultrasonic generator being an above-described ultrasonic generator.

Consequently, a lithotripsy device is provided, in which an optimal fragmentation performance of the sonotrode is obtainable by means of the ultrasonic vibration excitation means, despite an electrical and/or mechanical disruption.

In order to generate ultrasonic waves, the ultrasonic vibration excitation means comprises at least one piezo element between a proximally arranged counter bearing and a distally arranged horn, with the at least one piezo element being mechanically coupled to the counter bearing and the horn, and the horn being connectable to a holding unit of the sonotrode and/or the sonotrode.

Hence, the ultrasonic vibration excitation means and/or the at least one piezo element—two piezo elements are preferable—are operable in resonance with the horn and the sonotrode. In this case, the proximally arranged counter bearing functions as a reflector for the ultrasonic waves generated by the piezo element or the piezo elements.

In a further embodiment, an electrically conductive element which is electrically connected to the ultrasonic generator is arranged on the at least one piezo element and/or between two piezo elements.

On the one hand, this allows a mechanical deformation to be impressed on the piezo element or piezo elements by means of the transmitted AC voltage. On the other hand, the specific resonant frequency of the sonotrode can be measured by means of the measuring apparatus of the ultrasonic generator as a result of the electrical connection.

In order to provide a combined lithotripsy device with an additional shock excitation, the lithotripsy device comprises an acceleration tube with a cavity, a proximal end, and a distal end, and with a longitudinal center axis, a movable projectile within the cavity, a proximal-side abutment element, a distal-side abutment element, and a force generation apparatus for moving the projectile back and/or forth along an acceleration path between the proximal-side abutment element and the distal-side abutment element, with the sonotrode being excitable to vibrate as a result of mechanical impact of the projectile on the distal-side abutment element such that a combined vibration excitation of the sonotrode is realizable by means of the force generation apparatus and the at least one piezo element.

As a result, both the vibration excitation of the sonotrode by means of the ultrasonic vibration excitation means and the shock excitation of the sonotrode by means of the projectile can each have an optimal configuration and be operated with maximum fragmentation performance, without the shock excitation by means of the projectile and the generation of overvoltages at the at least one piezo element caused thereby disrupting the measuring apparatus of the ultrasonic generator and/or preventing a correction of the frequency.

In a further aspect of the invention, the object is achieved by a method for operating and/or controlling a lithotripsy device so as to avoid a disruption of an ultrasonic generator as a result of a projectile impact, the lithotripsy device comprising an above-described ultrasonic generator or being an above-described lithotripsy device, including the following steps:

supplying an AC voltage at a frequency to an ultrasonic vibration excitation means by means of the ultrasonic generator such that a vibration of the sonotrode is excited by means of the ultrasonic vibration excitation means, measuring time profiles of a voltage and current by means of the measuring unit and determining a frequency of the parallel resonant circuit in the measuring apparatus, determining the phases of the time profiles of the voltage and current, optionally adjusting the frequency by means of a phase locked loop unit until a phase shift of the time profiles of the voltage and current is zero or has reached a specified phase shift, storing the frequency in a data storing and/or data processing unit, implementing the shock excitation of the sonotrode by means of a projectile and supplying an AC voltage at the previously stored frequency to the ultrasonic vibration excitation means such that the ultrasonic generator is operated without a disruption resulting from the impact of the projectile.

This provides a method with which disruptions caused by the impact of the projectile and/or other mechanical and/or electronic disruptions are damped and filtered out within the ultrasonic generator on an electronic level. Should the measuring apparatus nevertheless be unable to measure plausible time profiles of the voltage and current despite damping and/or elimination of voltage peaks and consequently be unable to determine a phase shift for correcting the frequency, the previously stored frequency is used briefly during the disruption by virtue of an AC voltage at the previously stored frequency being supplied to the ultrasonic vibration excitation means during the disruption time period, with the result that the sonotrode is optimally excitable to vibrate by means of the ultrasonic vibration excitation means, without this impairing the application of the sonotrode by the user.

With regard to the claimed method, it should be stressed that this relates to the operation and control of the ultrasonic generator and hence of the lithotripsy device. However, this is restricted to the internal operation of the ultrasonic generator and lithotripsy device and does not comprise a method for using the sonotrode. The drawings, the description, and the claims contain numerous features in combination. It will be appreciated that the features mentioned above and the features yet to be explained below are applicable not only in the respectively specified combination but also in other combinations or on their own, without departing from the scope of the present invention.

BRIEF DESCRIPTION OF THE DRAWINGS

The invention is explained in more detail using exemplary embodiments. In the drawing:

FIG. 1 shows a very schematic illustration of a lithotripsy device having an ultrasonic generator and a connected ultrasonic transducer.

DETAILED DESCRIPTION

Figure 1:
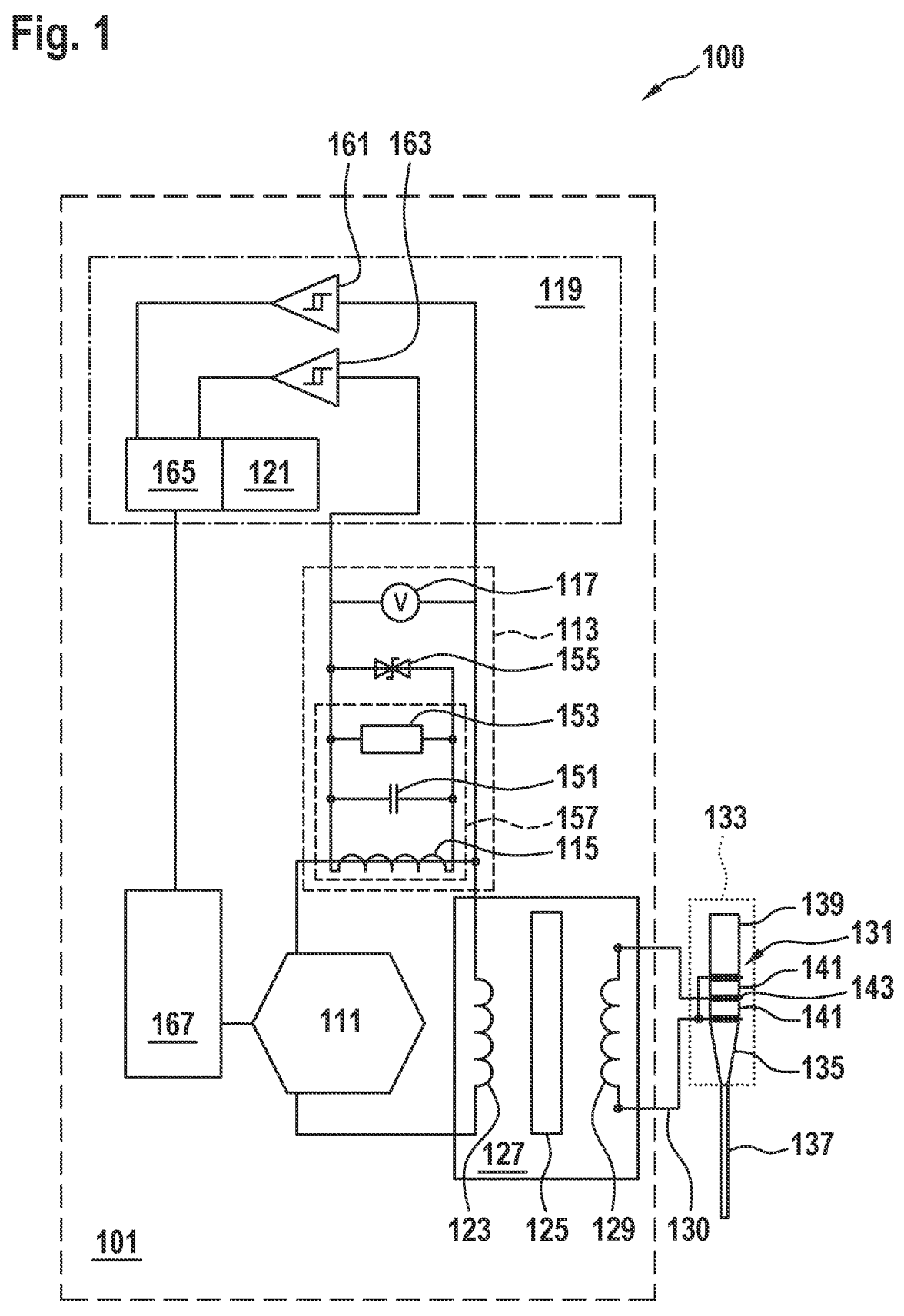
Figure 2:
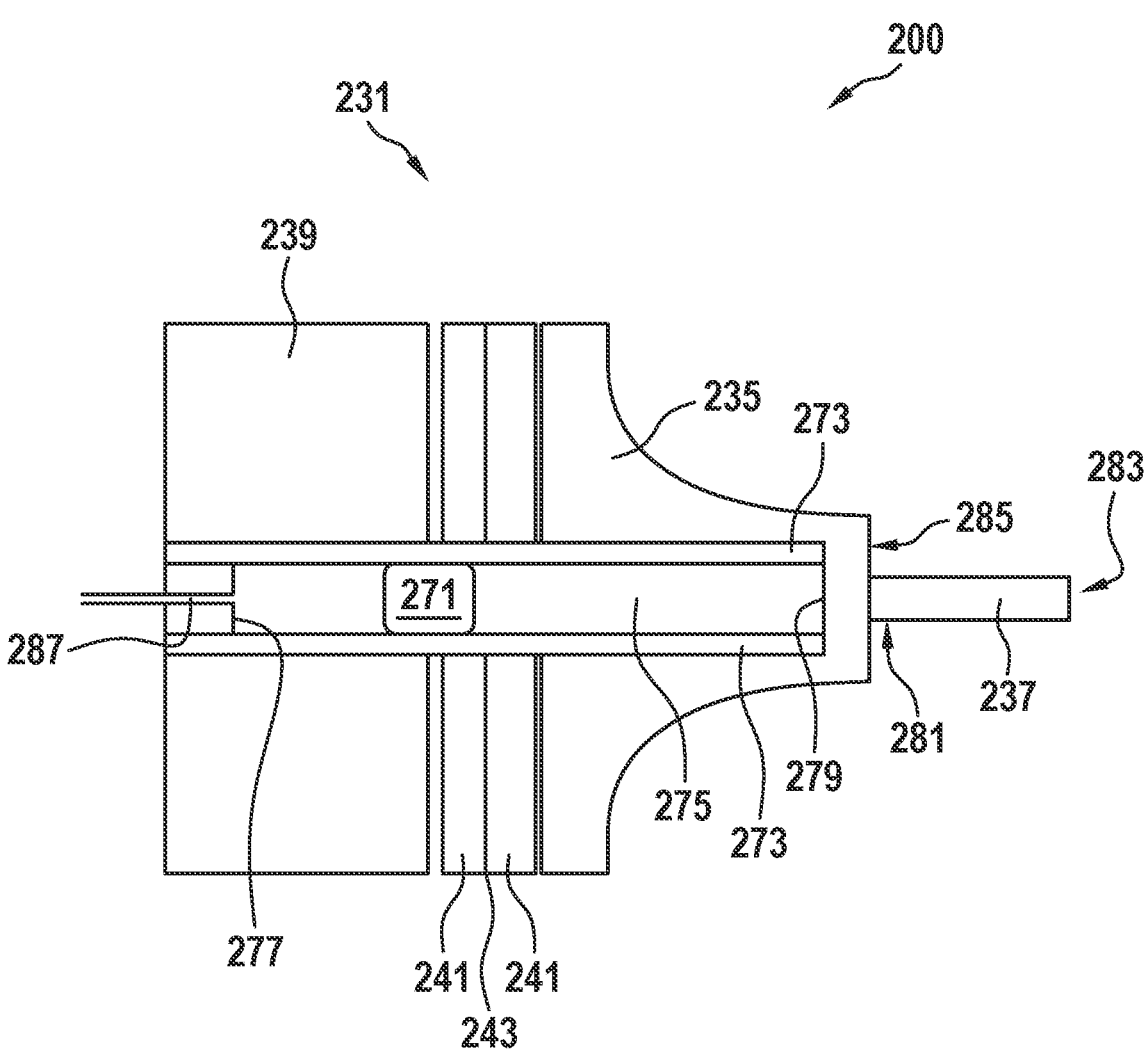
FIG. 2 shows a very schematic illustration of an alternative of a lithotripsy device having an ultrasonic transducer, an acceleration tube, and a projectile.

A lithotripsy device 100 comprises an ultrasonic generator 101 and an ultrasonic transducer 131, which are electrically interconnected by means of a high-voltage cable 130 (FIG. 1). The ultrasonic generator 101 comprises an oscillator 167, a sine-wave generator 111, a measuring apparatus 113, a closed-loop control apparatus 119, a data processing apparatus 121, and a transmitter 127.

The ultrasonic transducer 131 is in the form of a hand-piece 133. Alternatively, the transmitter 127 may also be arranged directly in the ultrasonic transducer 131 in the form of a handpiece 133, with the result that the high-voltage cable 130 is not required in this case.

A counter bearing 139 is arranged proximally in the interior of the handpiece 133 of the ultrasonic transducer 131, followed by two piezo elements 141 that are separated by a copper plate 143 and, to the distal side, a horn 135. A sonotrode 137 is arranged at the distal end face of the horn 135.

A power supply unit (not shown) of the ultrasonic generator 101 has an electrical isolation between a primary mains voltage (90 to 240 V AC) and a low voltage. From the low voltage, the sine-wave generator 111 generates an AC voltage as a low voltage 123 with a changeable amplitude and a changeable frequency ranging from 20 to 34 kHz. The transmitter 127 has an electrical isolation 125 between this AC voltage as a low voltage 123 and a transformed high voltage 129, for example 400 V, for operating the ultrasonic transducer 131, with the frequency ranging from 20 to 34 kHz set by the sine-wave generator 111 being maintained during the transmission. Upstream of the transmitter 127, a measuring apparatus 113 which has a respective channel for voltage measurement 117 and current measurement is arranged in a low-voltage 123 line. For the current measurement, the measuring apparatus 113 comprises a current measuring coil 115 and, in each case connected in parallel with the current measuring coil 115, a capacitor 151 and a resistor 153 which form a parallel resonant circuit 157 together with the current measuring coil 115. Moreover, a suppressor diode 155 is arranged in parallel with the parallel resonant circuit 157 and hence in parallel with the current measuring coil 115.

The measuring apparatus 113 is connected to the closed-loop control apparatus 119, by means of which the AC voltage 123 with the changeable amplitude and/or frequency generated by the sine-wave generator 111 is controllable. The closed-loop control apparatus 119 comprises a first Schmitt trigger 161 and a second Schmitt trigger 163, which are connected to a phase locked loop unit 165. Moreover, the closed-loop control apparatus 119 comprises the data processing apparatus 121. The phase locked loop unit 165 is connected to the oscillator 167 which in turn is connected to the sine-wave generator 111.

The following operations in a method for operating and controlling the ultrasonic generator 101 and the lithotripsy device 100 are realized by means of the ultrasonic generator 101 and the lithotripsy device 100:

Prior to the actual method, the ultrasonic transducer 131, and hence the sonotrode 137, is connected to the ultrasonic generator 101 by way of the high-voltage cable 130. In the first step 303 of the method 301, the AC voltage 123 at a frequency of 27.0 kHz generated by the sine-wave generator 111 is supplied via the transmitter 127 as a high voltage 129 to the piezo elements 141 via the copper plate 143. An ultrasonic vibration is induced on account of the deformation of the piezo elements 141 clamped between the proximal-side counter bearing 139 and the distal-side horn 135 caused thereby, whereby a resonant vibration of the connected sonotrode 137 is excited.

Figure 3:
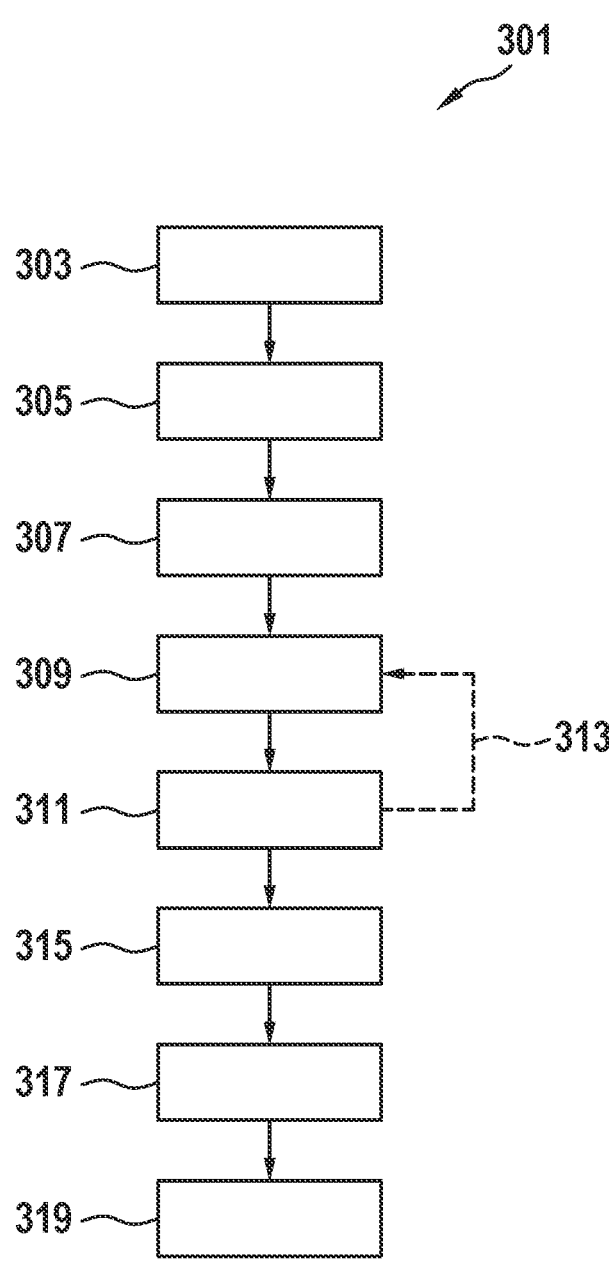
FIG. 3 shows a schematic illustration of a method for operating and controlling a lithotripsy device.

The measuring apparatus 113 is used to perform a continuous measurement 305 of time profiles of a voltage and current by means of the voltage measurement 117 and the current measuring coil 115 (FIG. 3). At the same time, a frequency of the parallel resonant circuit 157 of the measuring apparatus 113 is determined (step 307). The measured time profiles of the voltage and current are converted into rectangular signals in the closed-loop control apparatus 119 by means of the first Schmitt trigger 161 and second Schmitt trigger 163. Subsequently, the phases of the time profiles of the voltage and current are determined 309 by means of the phase locked loop unit 165 and the frequency is optionally adjusted 311 by means of the phase locked loop unit 165 until a phase shift of the time profiles of the voltage and current is zero, and there is optionally a repetition 313. The frequency determined at a phase shift of zero is stored in the data processing apparatus 121 (step 315).

In the case of a shock excitation 317 of the sonotrode 137 as a result of an impact of the projectile 271 on the proximal end of the counter bearing 139 (not shown in FIG. 1) or any other mechanical and/or electronic disruption and an overvoltage caused thereby, the back-transmitted voltage signal is initially damped in the measuring apparatus 113 by means of the resistor 153. For further interference suppression, the suppressor diode 155 for suppressing the overvoltage is connected before the measured signals are transmitted to the Schmitt triggers 161, 163. If the overvoltage is so high that the measuring apparatus 113 is unable to measure meaningful current and voltage values on account of the superposition and the phase shift is consequently not determinable, an AC voltage at the previously determined and stored frequency is supplied 319 to the ultrasonic transducer 131 from the data processing apparatus 121 in the next method step, with the result that the ultrasonic generator 101 is operated in a manner freed from the shock excitation and/or disruption.

In an alternative of a combined lithotripsy device 200, the ultrasonic transducer 231 comprises a counter bearing 239, two piezo elements 241 with a copper plate 243 arranged therebetween, and a horn 235. With its proximal end 281, a sonotrode 237 is arranged at a distal end 285 of the horn 235. The distal end 283 of the sonotrode 237 serves to fragment calculi and, in terms of length, is not depicted true to scale in FIG. 2. In its interior, the ultrasonic transducer 231 comprises a cavity, in which an acceleration tube 273 is arranged. A projectile 271 is arranged within a cavity 275 of the acceleration tube 273 so as to be movable between a proximal-side abutment element 277 and a distal-side abutment element 279. A compressed-air port 287 for introducing compressed air into the cavity 275 for the purpose of moving the projectile 271 is arranged to the proximal side of the proximal-side abutment element 277. As described above, the ultrasonic transducer 231 is connected to an ultrasonic generator 101. As described above, a high voltage 129 is applied to the piezo elements 241 which as a result of their deformation caused thereby instigate an excitation of vibrations in the sonotrode 237. Now, for additional shock excitation, compressed air is pushed into the cavity 275 of the acceleration tube 273 via the compressed-air port 287, whereby the projectile 271 is accelerated in the direction of the distal-side abutment element 279 and the impact on the distal-side abutment element 279 transmits a shock to the proximal end 281 of the sonotrode 237 via the distal end 285 of the horn 235, whereby the sonotrode 237 is excited to vibrate. Since the projectile 271 impacts on the distal-side abutment element 279 in the direct vicinity of the piezo elements 241, this impact also greatly affects the piezo elements 241, whereby these deform and generate a very high voltage. This very high voltage generated is transmitted back over the transmitter 127 to the ultrasonic generator 101 and disrupts the measuring apparatus 113. In the measuring apparatus 113, the resistor 153 and the suppressor diode 155 are only able to partly dampen and suppress this high voltage signal. As soon as the measuring apparatus 113 is no longer able to determine meaningful time profiles of current and voltage, a frequency previously stored in the data processing apparatus 121 is transmitted to the ultrasonic transducer 231 via the oscillator 167 and the sine-wave generator 111 as described above, with the result that the ultrasonic transducer 231 is operable with an optimal fragmentation performance of the sonotrode 237. Otherwise, the method for operating and controlling the ultrasonic generator 101 and the combined lithotripsy device 200 is implemented as described above.

Hence, an ultrasonic generator 101 and a lithotripsy device 100, 200 are provided, in which, during a combined operation with vibration excitation by means of the ultrasonic transducer 131, 231 and shock excitation by means of the projectile 271 of the sonotrode 137, 237, both excitations are operable with maximum fragmentation performance, with disruptions of the measuring apparatus 113 of the ultrasonic generator 101 as a result of the shock excitation initially being damped and eliminated by the measuring apparatus 113 itself and, in the case of a disruption signal that is too high, a previously determined frequency for the continued operation of the ultrasonic transducer 131, 231 being transferred to the latter by means of the closed-loop control apparatus 119 of the ultrasonic generator 101, without this impairing the vibration excitation.

The drawings, the description, and the claims contain numerous features in combination. It will be appreciated that the aforementioned features are applicable not only in the respectively specified combination but also in other combinations or on their own, without departing from the scope of the present invention. The invention relates to an ultrasonic generator for supplying an electrical power for fragmenting calculi, the ultrasonic generator being assignable a sonotrode, an ultrasonic vibration excitation means for exciting a vibration of the at least one sonotrode, and optionally a force generation apparatus for generating a force for moving a projectile for shock excitation of the sonotrode, with the ultrasonic vibration excitation means being excitable at a vibration frequency by means of the ultrasonic generator by supplying an AC voltage, and the ultrasonic generator comprising a measuring apparatus with at least one measuring unit for measuring a time profile of a voltage and/or current, and an open-loop and/or closed-loop control apparatus for adjusting an electrical power suppliable by the ultrasonic generator to the ultrasonic vibration excitation means, with the measuring apparatus comprising at least one resistor arranged in parallel with the measuring unit and optionally a capacitor arranged in parallel with the measuring unit, wherein the measuring apparatus comprises, in parallel with the at least one measuring unit, at least one suppressor diode for suppressing overvoltage. The invention also relates to a lithotripsy device and a method for operating and controlling a lithotripsy device.

LIST OF REFERENCE SIGNS

100 Lithotripsy device
101 Ultrasonic generator
111 Sine-wave generator
113 Measuring apparatus
115 Current measuring coil
117 Voltage measurement
119 Closed-loop control apparatus
121 Data processing apparatus
123 Low voltage (AC voltage)
125 Electrical isolation
127 Transmitter
129 High voltage
130 High-voltage cable
131 Ultrasonic transducer
133 Handpiece
135 Horn
137 Sonotrode
139 Counter bearing
141 Piezo element
143 Copper plate
151 Capacitor
153 Resistor
155 Suppressor diode
157 Parallel resonant circuit
161 First Schmitt trigger
163 Second Schmitt trigger
165 Phase locked loop unit
167 Oscillator
200 Lithotripsy device
231 Ultrasonic transducer
235 Horn
237 Sonotrode
239 Counter bearing
241 Piezo element
243 Copper plate
271 Projectile
273 Acceleration tube
275 Cavity
277 Proximal-side abutment element
279 Distal-side abutment element
281 Proximal end of the sonotrode
283 Distal end of the sonotrode
285 Distal end of the horn
287 Compressed-air port
301 Method for operating and controlling a lithotripsy device
303 Supplying an AC voltage at a frequency
305 Continuously measuring voltage and current
307 Determining a frequency of the parallel resonant circuit
309 Determining the phases
311 Adjusting the frequency
313 Repeat
315 Storing the frequency
317 Shock excitation of the sonotrode
319 Supplying an AC voltage at the frequency stored previously

The invention claimed is:

1. An ultrasonic generator configured to supply an AC voltage to an ultrasonic vibration excitor to generate a resonant vibration in a sonotrode which is configured for fragmenting calculi, the ultrasonic generator being assigned to the sonotrode, the ultrasonic vibration excitor configured to excite a vibration of the sonotrode, and a force generation apparatus configured to generate a force for moving a projectile for shock excitation of the sonotrode, with the ultrasonic vibration excitor being excited at a vibration frequency by the ultrasonic generator by supplying the AC voltage, the ultrasonic generator comprising:

a transmitter, an oscillator, a sine-wave generator, wherein the transmitter is configured to at least provide electrical isolation between a lower AC voltage from the sine-wave generator and a higher voltage for the ultrasonic vibration excitor, a phase locked loop unit, the a phase locked loop unit being connected to the oscillator that is connected to the sine-wave generator configured to generate the AC voltage for the ultrasonic vibration excitor, and a measuring apparatus with at least one measuring unit configured to measure a time profile of a voltage and/or current, and an open-loop and/or closed-loop control apparatus, that is a phase locked loop unit, configured to adjust an electrical power supplied by the ultrasonic generator to the ultrasonic vibration excitor, with the measuring apparatus comprising at least one resistor arranged in parallel with the at least one measuring unit and a capacitor arranged in parallel with the measuring unit, wherein the measuring apparatus comprises, in parallel with the at least one measuring unit, at least one suppressor diode configured to suppress overvoltage.

2. The ultrasonic generator as claimed in claim 1, wherein the at least one measuring unit is a measuring coil and the measuring apparatus comprises the capacitor to form a parallel resonant circuit and the resistor for damping a time profile of the voltage and/or current.

3. The ultrasonic generator as claimed in claim 1, wherein the at least one measuring unit is a measuring resistor configured to measure the time profile of the current.

4. The ultrasonic generator as claimed in claim 2, wherein the capacitor and the at least one measuring unit are configured wherein the parallel resonant circuit has a frequency ranging from 20 kHz to 40 kHz.

5. The ultrasonic generator as claimed in claim 1, wherein the open-loop and/or closed-loop control apparatus comprises two comparators configured to generate rectangular signals from the time profile of the current and voltage.

6. The ultrasonic generator as claimed in claim 1, wherein the ultrasonic generator comprises a data storing and/or data processing unit, in which a previously determined frequency or resonant frequencies of the assigned sonotrode is or are storable.

7. The ultrasonic generator as claimed in claim 1, wherein the open-loop and/or closed-loop control apparatus comprises the phase locked loop unit such that the supplied electrical power and/or the frequency are or is adjusted by the open-loop and/or closed-loop control apparatus such that a phase shift of the time profiles of the voltage and current is zero or has a specified value and/or, in the case of a shock excitation of the sonotrode by the projectile, the previously determined frequency and/or resonant frequency of the supplied electrical power is specified.

8. A lithotripsy device configured to fragment and/or removing calculi, with the lithotripsy device comprising:

the ultrasonic generator, a carrier unit with an ultrasonic vibration excitor, and the sonotrode that is connected distally to the carrier unit, the ultrasonic generator being electrically connected to the carrier unit, wherein the ultrasonic generator is an ultrasonic generator as claimed in claim 1.

9. The lithotripsy device as claimed in claim 8, wherein the ultrasonic vibration excitor comprises at least one piezo element between a proximally arranged counter bearing and a distally arranged horn, with the at least one piezo element is mechanically coupled to the counter bearing and the horn, and the horn being connected to a holding unit of the sonotrode and/or the sonotrode.

10. The lithotripsy device as claimed in claim 8, wherein an electrically conductive element which is electrically connected to the ultrasonic generator is arranged on the at least one piezo element and/or between two piezo elements.

11. The lithotripsy device as claimed in claim 8, wherein the lithotripsy device comprises an acceleration tube with a cavity, a proximal end, and a distal end, and with a longitudinal center axis, a moving projectile within the cavity, a proximal-side abutment element, a distal-side abutment element, and a force generation apparatus configured to move the projectile back and/or forth along an acceleration path between the proximal-side abutment element and the distal-side abutment element, with the sonotrode being excited to vibrate as a result of mechanical impact of the projectile on the distal-side abutment element such that a combined vibration excitation of the sonotrode is realized by the force generation apparatus and the at least one piezo element.

12. A method to operate and/or control a lithotripsy device so as to avoid a disruption of an ultrasonic generator as a result of a projectile impact, the lithotripsy device comprising an ultrasonic generator the method comprising:

supplying an AC voltage at a frequency to an ultrasonic vibration excitor by the ultrasonic generator such that a vibration of a sonotrode is excited by the ultrasonic vibration excitor, wherein the AC voltage is supplied via a transmitter, an oscillator, and a sine-wave generator, wherein the transmitter provides electrical isolation between a lower AC voltage from the sine-wave generator and a higher voltage for the ultrasonic vibration excitor, measuring time profiles of a voltage and current by measuring units and determining a frequency of a parallel resonant circuit in the measuring units, and suppressing overvoltage by at least one suppressor diode in parallel with the measuring unit wherein a measuring apparatus includes at least one resistor in parallel with the measuring units and a capacitor in parallel with the measuring units, determining phases of the time profiles of the voltage and current, adjusting the frequency by a phase locked loop unit until a phase shift of the time profiles of the voltage and current is zero or has reached a specified phase shift, storing the frequency in a data storing and/or data processing unit, and implementing the shock excitation of the sonotrode by a projectile and supplying an AC voltage at the previously stored frequency to the ultrasonic vibration excitor such that the ultrasonic generator is operated without a disruption resulting from an impact of the projectile.

* * * * *